United States Patent [19]

Hennig et al.

[11] 4,419,295

[45] Dec. 6, 1983

[54] CONTINUOUS PROCESS FOR THE PRODUCTION OF ORGANIC ISOCYANATES

[75] Inventors: Hans-Joachim Hennig, Leverkusen; Jürgen Lahrs, Cologne; Dietrich Liebsch, Leverkusen, all of Fed. Rep. of Germany

[73] Assignee: Bayer Aktiengesellschaft, Leverkusen, Fed. Rep. of Germany

[21] Appl. No.: 379,822

[22] Filed: May 20, 1982

[30] Foreign Application Priority Data

May 27, 1981 [DE] Fed. Rep. of Germany ....... 3121036

[51] Int. Cl.$^3$ .......................................... C07C 118/02
[52] U.S. Cl. .............................................. 260/453 PH
[58] Field of Search ................................. 260/453 PH

[56] References Cited

U.S. PATENT DOCUMENTS

| | | | |
|---|---|---|---|
| 3,507,626 | 4/1970 | Van Horn | 200/453 PH |
| 3,781,320 | 12/1973 | Irwin | 260/453 |
| 3,978,108 | 8/1976 | Teisseire et al. | 260/468 |
| 4,289,732 | 9/1981 | Bauer et al. | 260/453 PH X |
| 4,292,255 | 9/1981 | Hennig et al. | 260/453 AR |

FOREIGN PATENT DOCUMENTS

| | | |
|---|---|---|
| 1768439 | 4/1974 | Fed. Rep. of Germany . |
| 1792660 | 9/1977 | Fed. Rep. of Germany . |
| 2325637 | 4/1977 | France . |
| 901377 | 7/1962 | United Kingdom . |
| 1341311 | 12/1973 | United Kingdom . |
| 2036586 | 7/1980 | United Kingdom . |

*Primary Examiner*—Dolph H. Torrence
*Attorney, Agent, or Firm*—Gene Harsh; Joseph C. Gil; Lyndanne M. Whalen

[57] ABSTRACT

Organic mono- or poly-isocyanates are produced on a continuous basis by phosgenating the corresponding amines. A solution of the amine to be phosgenated is continuously sprayed through a smooth-jet nozzle into a solution of phosgene continuously flowing through a mixing chamber. The mixing chamber is maintained at a temperature of 120° to 300° C. and a pressure of from 10 to 1000 bars. The molar ratio of phosgene to primary amino groups is generally from 2:1 to 30:1.

9 Claims, 2 Drawing Figures

4,419,295

CONTINUOUS PROCESS FOR THE PRODUCTION OF ORGANIC ISOCYANATES

BACKGROUND OF THE INVENTION

This invention relates to a continuous process for the production of organic mono- or poly-isocyanates by continuous phosgenation of the primary amines on which the isocyanates are based.

It is known that organic isocyanates can be produced continuously by reacting primary amines with phosgene at elevated temperature and pressure. In German Offenlegungsschrift No. 2,252,068, e.g., production of isocyanates at super atmospheric pressures is described. In this process, the required isocyanate is used as solvent for the phosgene required. In German Auslegeschrift No. 1,768,439, a process in which amine solution is reacted with pure phosgene under similar temperature and pressure conditions is disclosed. And in German Offenlegungsschrift No. 2,404,773, primary amines are reacted with phosgene under pressure in the absence of solvents, (i.e., phosgene acts as the solvent).

Since the reaction of a primary amine with phosgene is an extremely fast reaction, the degree of mixing of these materials has a direct effect upon the reaction time and upon the yield of isocyanate. Methods of combining these two reaction components have therefore been investigated by those in the art. U.S. Pat. No. 3,781,320, for example, describes a special annular-gap mixer for combining these materials. French Pat. No. 7,628,343 describes a mixer which imparts a circulating and oppositely directed movement to the flow of at least one component. A process for mixing two liquids (particularly an amine with a phosgene solution), in which fan-shaped jets are used, is described in German Offenlegungsschrift No. 2,950,216; and German Offenlegungsschrift No. 1,792,660 describes an apparatus for mixing two streams of liquid reactants in which the streams are combined at an acute angle.

SUMMARY OF THE INVENTION

It is an object of the present invention to provide a continuous process for the production of isocyanates in a single-stage reaction.

It is also an object of the present invention to provide a continuous process for the production of isocyanates which results in greatly improved volume/time yields and product yields.

It is a further object of the present invention to provide a continuous process for the production of isocyanates in which virtually no secondary reactions occur and which may be carried out using technically simple apparatus.

It is yet another object of the present invention to provide a continuous process for the production of isocyanates in which substantially no by-products which could block the pipes of the apparatus employed are formed.

These and other objects which will become apparent to those skilled in the art are accomplished by continuously combining a primary amine solution with a phosgene solution in a mixing chamber at elevated temperature and pressure in quantities such that less than a stoichiometric quantity of amine is present.

The amine solution is sprayed into the phosgene solution by means of at least one jet nozzle having an internal diameter of from 0.01 to 30 mm and having a differential pressure of 0.5 bar. The components of the solution leaving the mixing chamber are continuously separated.

DETAILED DESCRIPTION OF THE INVENTION

The present invention relates to a process for the continuous production of organic mono- or poly-isocyanates in a single-stage reaction by continuously combining solutions of primary mono- or poly-amines in inert organic solvents with excess quantities of phosgene dissolved in an inert organic solvent. The amine and phosgene solutions are combined at elevated temperature and pressure in a mixing chamber (4). The combined solutions continuously leaving the mixing chamber are continuously worked up, optionally after they have passed from the mixing chamber through a reaction zone. The phosgene component used in excess is continuously introduced into the mixing chamber while the amine component (used in a substoichiometric quantity) is sprayed into the phosgene solution by means of at least one smooth-jet nozzle (2) having an internal diameter of from 0.01 to 30 mm. A differential pressure between the pressure of the amine solution (before entering the nozzle) and the pressure of the phosgene in the mixing chamber of at least 0.5 bar should be maintained.

The process of the present invention and the mixing apparatus in which it may be carried out will be described with reference to FIGS. 1 and 2.

Figure 1:
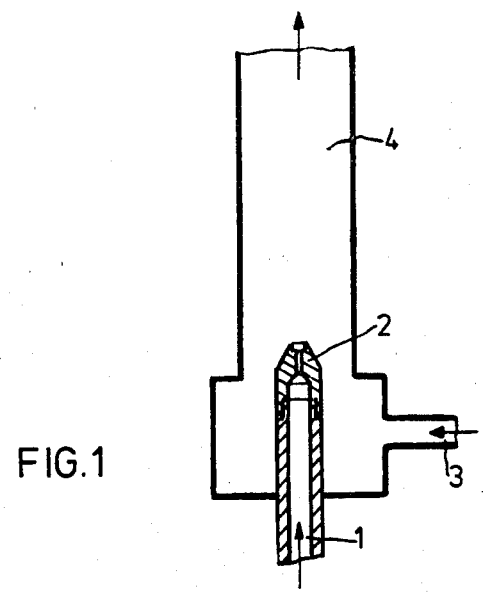
FIG. 1 shows a mixing chamber suitable for the practice of the present invention.

FIG. 1 shows a mixing chamber provided with a smooth-jet nozzle. In FIG. 1, (1) represents the pipe for the amine solution leading into the mixing chamber; (2) represents the smooth-jet nozzle; (3) represents the pipe for the phosgene solution leading to the mixing chamber; and (4) represents the mixing chamber.

Figure 2:
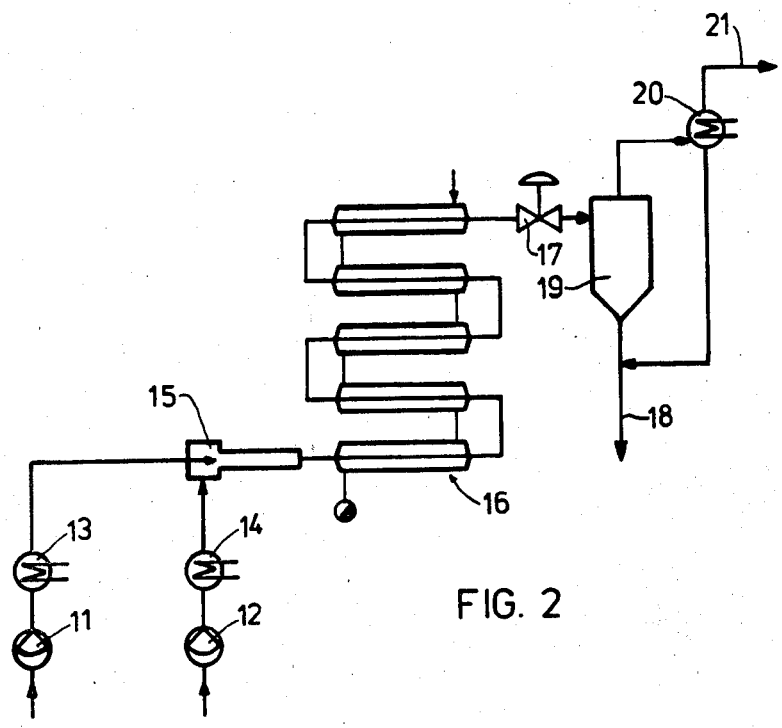
FIG. 2 is a diagram of an apparatus suitable to the practice of the present invention.

FIG. 2 shows a diagram of one apparatus suitable for carrying out the process according to the invention. In FIG. 2, (11) represents a pump for the amine solution; (12) represents a pump for the phosgene solution; (13) represents a heat exchanger suitable for heating the amine solution; (14) represents a heat exchanger suitable for heating the phosgene solution; (15) represents a mixing chamber provided with a smooth-jet nozzle of the type shown in FIG. 1; (16) represents a heatable tube reactor following the mixing chamber; (17) represents an expansion valve; (18) represents the outlet for the isocyanate solution; (19) represents an expansion vessel; (20) represents a condenser; and (21) represents the outlet for the gas phase formed.

The process of the present invention is suitable for phosgenating any primary mono- or poly-amines, particularly in the production of polyisocyanates commonly used in polyurethane chemistry. Starting materials for the process of the present invention are 3 to 95 wt. % (preferably 20 to 75 wt. %) phosgene solutions in suitable solvents, and 5 to 95 wt. % (preferably 5 to 50 wt. %) solutions of mono- or poly-amines in suitable solvents. Amines suitable for use in the process of the present invention include: methylamine, ethylamine; butylamine, stearylamine; phenylamine; p-tolylamine; 1,4-diaminobutane; 1,6-diaminohexane; 1,8-diaminooctane; 1,4-diaminobenzene; 2,4-diaminotoluene; 2,6-diaminotoluene; mixtures of the last two isomers; 2,2'-diaminodiphenyl methane; 2,4'-diaminodiphenyl methane; 4,4'-diaminodiphenyl methane; mixtures of the last three isomers; alkyl-substituted diamines of the diphenyl methane series (such as 3,4'-diamino-4-methyl diphenyl methane); polyamine mixtures of the diphenyl methane series of the type obtained in known manner by condensing aniline with formaldehyde; p-xylylene diamine; perhydrogenated 2,4- and/or 2,6-diaminotoluene; 2,2'-, 2,4'- and/or 4,4'-diaminodicyclohexyl methane; 1-amino-3,3,5-trimethyl-5-aminomethyl cyclohexane (isophorone diamine, IPDA in short); lysine ethyl ester; glysine aminoethyl ester and 1,6,11-triaminoundecane.

Solvents which may be used for making the phosgene and amine solutions of the present invention are any solvents which are inert under the reaction conditions. Examples of such solvents are chlorobenzene, o-dichlorobenzene, toluene, xylene, methylene chloride, perchloroethylene, trichlorofluoromethane and butyl acetate. Chlorobenzene or o-dichlorobenzene are preferred solvents. Mixtures of any of the above-listed solvents may also be used. It is preferable, although not essential, to use the same solvent or solvent mixture for the amine component and the phosgene.

In the process of the present invention, the phosgene and amine solutions should be used in quantities such that a molar ratio of phosgene to primary amino groups of from about 2:1 to 30:1, preferably from 3:1 to 18:1 prevails in the mixing chamber.

The way in which the reactants are combined is critical to the invention. To this end, a mixing chamber provided with a smooth-jet nozzle of the type illustrated in FIG. 1 is used. The smooth-jet nozzle should generally have an internal diameter of from 0.1 to 30 mm, preferably from 0.5 to 15 mm, and a length of at least 0.1 mm, preferably from 1 to 15 mm. The length-to-diameter ratio should amount to at least 1:1. The internal diameter of the mixing chamber should generally be at least 10 times (preferably between 50 and 300 times) the internal diameter of the smooth-jet nozzle, so that the distance between the jet issuing from the nozzle and the side wall of the mixing chamber amounts to at least 5 times the internal diameter of the nozzle. The distance from the nozzle exit to the opposite boundary of the mixing chamber (or the reaction zone following the mixing chamber, if any) should be at least 10 times, preferably at least 100 times the nozzle diameter to ensure that the jet issuing from the nozzle is able to penetrate freely into the phosgene solution from boundaries of the mixing zone facing the nozzle.

The process of the present invention may also be carried out using a mixing chamber which comprises several smooth-jet nozzles of the above-described type arranged in parallel instead of a single smooth-jet nozzle. In this case, the smooth-jet nozzles are arranged in such a way that the jets of amine solution leaving the nozzle penetrate parallel to one another into the phosgene solution already present in the mixing chamber. These jets should also be positioned so that the interval between the individual jets and the interval between the outer jet(s) and the side wall of the mixing chamber is at least 10 times the nozzle diameter. It is also possible to use jets having different internal diameters arranged in parallel in carrying out the process of the present invention. However, the process is preferably carried out using a mixing apparatus which has only one smooth-jet nozzle.

In the process of the present invention, the mixing vessel and the reaction zone following the mixing vessel (if used) are continuously charged with phosgene solution heated to between 120° and 300° C., preferably to between 150° and 250° C. The outlet valve should generally be adjusted in such a way that a pressure of 10 to 1000 bars (preferably from 25 to 150 bars) prevails in the mixing vessel and the reaction zone optionally following the mixing vessel. Use of such pressures ensures that the phosgene solution flows continuously through and completely fills the mixing vessel in a single phase, i.e. without the formation of gas bubbles. However, the outlet valve may also be adjusted in such a way that the reaction mixture (in particular the hydrogen chloride formed) is partly present in the gas phase so that a two-phase system is present (particularly in the reaction zone following the mixing chamber). The passage of two-phase mixtures through the tube reactors of the reaction zone promotes additional intensive mixing of the reactants. However, the pressure must be adjusted so that the amine solution leaving the nozzle penetrates into a liquid phosgene solution. The amine solution is generally sprayed into the phosgene solution flowing continuously into the mixing chamber under the above-mentioned pressure and temperature conditions by means of the smooth-jet nozzle(s) while a differential pressure of at least 0.5 bar, preferably from 1 to 200 bars and, most preferably, from 3 to 50 bars is maintained. In other words, the pressure built up by the pump for the amine solution (before entering the nozzle) must be higher than the pressure built up by the pump for the phosgene solution in the mixing chamber.

The introduction of the amine solution into the phosgene solution at high speed in the form of an extremely fine jet (as made possible by a smooth-jet nozzle) ensures intensive mixing of the components and, at the same time, their reaction. The quality of mixing, which has a direct bearing on the reaction and hence on the yield of isocyanate, is greatly influenced by the magnitude of the differential pressure under which the amine solution is sprayed into the phosgene solution under pressure. It is the magnitude of the differential pressure which determines the speed at which the fine amine jet enters the phosgene solution.

The pressure of the amine solution with respect to the pressure of the phosgene solution (i.e. the differential pressure of the two components) should be selected within the above-mentioned limits in such a way that the sprayed amine solution enters the phosgene solution already present in the mixing chamber at a relative velocity of more than 5 m/second. Systems in which starting materials react very quickly with one another (as is the case with a primary amine and phosgene) requires mixing of the very highest quality which mixing is obtained by a high shear gradient. Therefore, the ratio between the respective velocities of the liquids flowing i parallel current but at different speeds (i.e. under shearing conditions) should be at least 5:1. Such shearing conditions may be obtained when differential pressures within the above-mentioned limits are employed.

The temperature of the amine solution to be sprayed is not critical because the temperature prevailing in the mixing vessel (and in the reaction zone optionally following the mixing vessel) is determined primarily by the temperature of the phosgene solution present in excess, by the heat of reaction of the exothermic phosgenation reaction and by the external heating of the reaction zone optionally following the mixing chamber. In general, the amine solution is preheated to between about 20° and 180° C., preferably to between 50° and 150° C. The sole requirement is that a temperature of 120° to 300° C. and preferably from 150° to 250° C. should prevail in the mixing vessel and in the reaction zone if used. Under these temperature conditions, the sprayed amine is spontaneously phosgenated in a single stage so that (in extreme cases) the mixing vessel may perform the dual function of a mixing and reaction vessel. However, if the mixing vessel is not to be followed by another reaction zone, the dimensions of the mixing vessel should preferably be such that the distance between the nozzle exit and the boundary of the mixing vessel opposite the nozzle amounts to at least 200 times the nozzle diameter.

In many cases, it is advantageous for the mixing vessel to be followed by another reaction zone. Such a reaction zone may be made of tubular reactors, multiple-tube reactors or other conventional reactors, such as reaction vessels in series. This further reaction zone optionally connected to the outlet of the mixing vessel (shown in FIG. 2) may be provided with a jacket to enable the reaction zone to be heated. The reaction zone may of course also be heated in other ways.

In the process of the present invention, the phosgenation reaction is generally over after an average residence time of from 5 seconds to 5 minutes in the mixing vessel and the reaction zone optionally following the mixing vessel. To work up the reaction mixture, the reaction mixture leaving the mixing vessel and the optional reaction zone is generally expanded in a single stage through the outlet valve. A reduction in temperature of around 50° to 150° C. generally results from the release of this pressure. However, expansion to atmospheric pressure may also take place in two or more stages in order to keep the quantities of gas in each stage as small as possible. The mixture leaving the outlet valve is separated into a gaseous phase and a liquid phase in an expansion vessel. In the production or organic mono- or poly-isocyanates having a boiling point at atmospheric pressure of at least 100° C., the gas phase consists primarily of excess phosgene and hydrogen chloride formed during the phosgenation reaction. Small quantities of entrained solvent and isocyanate may be removed from the gas phase by fractional condensation in a suitable condenser. The condensate may be combined with the liquid phase accumulating in the expansion vessel. The liquid phase is worked up in known manner by distillation so that the monoisocyanate or polyisocyanate is obtained in pure form. The above-described method of working up the reaction mixtures accumulating in the process according to the invention is of course only one of several possible variants. The manner in which the reaction product mixtures are worked up is not critical and may be carried out by conventional methods.

The following Examples illustrating the process of the present invention are carried out in an apparatus of the type shown in FIG. 2. The mixing chamber (15) is used in combination with a following tube reactor. All of the percentages given in these examples are percentages by weight, unless otherwise indicated.

EXAMPLES

EXAMPLE 1

A 15% 1,6-diaminohexane solution in o-dichlorobenzene was fed into the mixing chamber at a rate of 36.6 kg/h. A 44.6% phosgene solution in o-dichlorobenzene was fed into the mixing chamber at a rate of 120 kg/h. These solutions were continuously reacted in a tubular mixing vessel (15) having an internal diameter of 25 mm and in a tube reactor (total volume of mixing vessel and tube reactor 7.3 liters). Mixing of the phosgene solution (heated to 180° C.) with the amine solution (heated to 130° C.) was achieved by spraying the amine solution through a smooth-jet nozzle (2) having an internal diameter of 0.5 mm and a length of 3 mm into the mixing vessel which was filled (without any bubbles) by the phosgene solution continuously introduced. The distance between the nozzle and the opposite outlet opening (connected to the tube reactor) of the mixing vessel was 30 cm. The distance between the nozzle jet and the side wall of the mixing vessel was 12.25 mm. The mixing vessel, the tube reactor and the phosgene solution were under a pressure of 60 bars. At the entrance to the smooth-jet nozzle, the amine solution was under a pressure of 81 bars. Reaction mixture was continuously removed from the tube reactor through the outlet valve (17) and separated in the separator (19) into a gas phase (21) and a liquid phase (18). Entrained fractions of liquid constituents were removed from the gas phase by fractional condensation in the condenser (20) and returned to the liquid phase.

Working up of the combined liquid phase by distillation gave 7.83 kg/h of 1,6-diisocyanatohexane, corresponding to a yield of 98.5%, based on the diamine used.

EXAMPLE 2

The procedure of Example 1 was repeated except that a pressure of 30 bars was maintained in the mixing and reaction zones and the pressure of the amine solution before entering the smooth-jet nozzle was 58 bars. The yield of 1,6-diisocyanatohexane was 7.7 kg/h, corresponding to 97% of the theoretical yield.

EXAMPLE 3

The apparatus used was the same as that used in Example 1, except that the volume of the tube reactor was such that the total volume of the mixing chamber and the tube reactor was only 0.9 liter. The nozzle diameter was 0.5 mm.

40 kg/h of a 17.8% of 1,6-diaminohexane solution in o-dichlorobenzene (preheated to 140° C.) were reacted as in Example 1 with 120 kg/h of a 61.7% phosgene solution in o-dichlorobenzene (preheated to 210° C.) under a reactor pressure of 60 bars. The amine solution was kept at a pressure of 80 bars before entering the nozzle. The reaction temperature in the mixing zone and in the following reaction zone was kept at 220° C. 1,6-diisocyanatohexane was obtained in a yield of 9.91 kg/h, corresponding to 96% of the theoretical yield, based on the diamine used.

EXAMPLE 4

54 kg/h of a 16.8% 1,6-diaminohexane solution in o-dichlorobenzene (preheated to 100° C.) were reacted as in Example 3 with 108 kg/h of a 43.9% phosgene solution (preheated to 200° C.). The nozzle diameter was 0.5 mm. The reactor pressure was 60 bars and the pressure of the amine solution before entering the nozzle was 88 bars. The temperature in the mixing and reaction zone was 221° C. 1,6-diisocyanatohexane was obtained in a yield of 12.3 kg/h, corresponding to 93.8% of the theoretical yield.

EXAMPLE 5

The apparatus used in this Example was the same as the apparatus used in the preceding Examples, except that the volume of the tube reactor following the mixing vessel was such that the total volume of the mixing vessel and the tube reactor was 1.55 liters. The nozzle had a diameter of 0.4 mm.

33 kg/h of a 22% 1,6-diaminohexane solution in o-dichlorobenzene (preheated to 135° C.) were reacted with 123 kg/h of a 62.2% phosgene solution in o-dichlorobenzene (preheated to 190° C.). The pressure prevailing in the mixing and reaction zone was 50 bars. The pressure of the amine solution before entering a nozzle was 75 bars. The temperature prevailing in the mixing and reaction zone was approximately 200° C. 1,6-diisocyanatohexane was obtained in a yield of 9.89 kg/h, corresponding to 94.9% of the theoretical yield.

EXAMPLE 6

The apparatus described in Example 1 was used with the same dimensions, except that the nozzle had a diameter of 0.5 mm.

53.6 kg/h of an 18% solution of 4,4'-diaminodiphenyl methane in chlorobenzene (preheated to 160° C.) were reacted with 96.4 kg/h of a phosgene solution in chlorobenzene (preheated to 190° C.). The pressure prevailing in the mixing and reaction zone was 65 bars. The pressure of the amine solution before entering the nozzle was 95 bars. 4,4'-diisocyanatodiphenyl methane accumulated in a yield of 11.7 kg/h, corresponding to 96% of the theoretical yield.

EXAMPLE 7

The apparatus used was the same as in the preceding Examples, except that the volume of the tube reactor was such that the total volume of the mixing chamber and the following reaction zone was 3.7 liters. The nozzle had a diameter of 0.4 mm.

42.2 kg/h of a 46.7% solution (preheated to 170° C.) of a mixture of 2,4-diaminotoluene and 2,6-diaminotoluene in a weight ratio of 1.86:1 in o-dichlorobenzene were reacted with 123.6 kg/h of an 80% solution of phosgene in o-dichlorobenzene (preheated to 216° C.). The pressure in the mixing and reaction zone was 60 bars. The pressure of the amine solution before entering the nozzle was 110 bars. The temperature in the mixing and reaction zone was 198° C. A mixture of 2,4- and 2,6-diisocyanatotoluene was obtained in a yield of 16.8 kg/h, corresponding to 97% of the theoretical yield.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous process for the production of an isocyanate comprising:
    (a) continuously combining a solution of a primary amine in an inert organic solvent with an excess of phosgene dissolved in an inert organic solvent in a mixing chamber at elevated temperature and pressure in a manner such that a less than stoichiometric quantity of amine is sprayed into the phosgene solution by means of at least one smooth jet nozzle having an internal diameter of from 0.01 to 30 mm and that a pressure differential of at least 0.5 bar is maintained; and
    (b) continuously separating the components of the solution leaving the mixing chamber.

2. The process of claim 1 wherein the solution leaving the mixing chamber is passed through a reaction chamber before the components are separated.

3. The process of claim 2 wherein the reaction chamber is maintained at a pressure of from 25 to 150 bars.

4. The process of claim 2 wherein the reaction chamber is maintained at a temperature of from 120° to 300° C.

5. The process of claim 1 wherein step (a) is carried out at a pressure of from 10 to 1000 bars.

6. The process of claim 1 wherein step (a) is carried out at a pressure of from 25 to 150 bars.

7. The process of claim 1 wherein the mixing chamber is maintained at a temperature of from 120° to 300° C.

8. The process of claim 1 wherein the mixing chamber is maintained at a temperature of from 150° to 250° C.

9. The process of claim 1 wherein the amine and phosgene solutions are combined in quantities such that the molar ratio of phosgene to primary amino groups is from 2:1 to 30:1.

* * * * *